(12) United States Patent
Yoshioka et al.

(10) Patent No.: US 9,594,242 B2
(45) Date of Patent: Mar. 14, 2017

(54) LIGHT SOURCE DEVICE FOR ENDOSCOPE SYSTEM

(71) Applicant: FUJIFILM Corporation, Tokyo (JP)

(72) Inventors: Masato Yoshioka, Ashigarakami-gun (JP); Eiji Oohashi, Ashigarakami-gun (JP); Hiroshi Shibuya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 135 days.

(21) Appl. No.: 14/630,839

(22) Filed: Feb. 25, 2015

(65) Prior Publication Data

US 2015/0241687 A1 Aug. 27, 2015

(30) Foreign Application Priority Data

Feb. 26, 2014 (JP) .................................. 2014-035959

(51) Int. Cl.
*G02B 23/24* (2006.01)
*A61B 1/00* (2006.01)
(Continued)

(52) U.S. Cl.
CPC ...... *G02B 23/2469* (2013.01); *A61B 1/00126* (2013.01); *A61B 1/00128* (2013.01); *A61B 1/0669* (2013.01); *A61B 1/07* (2013.01)

(58) Field of Classification Search
CPC ............ G02B 23/2469; A61B 1/00126; A61B 1/00128; A61B 1/0669; A61B 1/07
(Continued)

(56) References Cited

U.S. PATENT DOCUMENTS 6,231,503 B1 * 5/2001 Sugimoto ................ A61B 1/07
362/574
8,517,922 B2 8/2013 Koitabashi et al.
(Continued)

FOREIGN PATENT DOCUMENTS

JP 8-19517 A 1/1996
JP 3089950 B2 9/2000
(Continued)

OTHER PUBLICATIONS

Japanese Office Action, dated Jan. 27, 2016, for Japanese Application No. 2014-035959, with an English machine translation.
(Continued)

*Primary Examiner* — Evan Dzierzynski
(74) *Attorney, Agent, or Firm* — Birch, Stewart, Kolasch & Birch, LLP

(57) ABSTRACT

A light source device for an endoscope system comprises a light source unit, which collects light with a lens and allows the collected light to enter a light guide provided to an endoscope. The light source device comprises a receiving unit and a lens barrel (movable unit). The receiving unit receives insertion of the light guide. The receiving unit is attached to the lens barrel. The lens barrel moves in a direction perpendicular to a direction of the insertion of the light guide, in accordance with a force received by the receiving unit from the light guide. The light source unit applies collimated light to the lens. The lens is attached to the lens barrel and moves together with the receiving unit and the lens barrel, and makes at least a part of the collimated light enter the light guide.

7 Claims, 13 Drawing Sheets

(51) Int. Cl.
*A61B 1/06* (2006.01)
*A61B 1/07* (2006.01)

(58) Field of Classification Search
USPC .......................................................... 362/574
See application file for complete search history.

(56) References Cited

U.S. PATENT DOCUMENTS

| | | | | |
|---|---|---|---|---|
| 2001/0025135 | A1* | 9/2001 | Naito | A61B 1/00137 |
| | | | | 600/156 |
| 2007/0088198 | A1* | 4/2007 | Koitabashi | A61B 1/07 |
| | | | | 600/136 |
| 2008/0247059 | A1* | 10/2008 | Dong | G02B 7/102 |
| | | | | 359/696 |
| 2014/0142390 | A1* | 5/2014 | Bromwich | A61B 1/00126 |
| | | | | 600/160 |

FOREIGN PATENT DOCUMENTS

| | | |
|---|---|---|
| JP | 2006-87764 A | 4/2006 |
| JP | 2006-158859 A | 6/2006 |
| JP | 5277187 B2 | 8/2013 |
| JP | 2015-136545 A | 7/2015 |

OTHER PUBLICATIONS

Extended European Search Report, dated Jun. 29, 2015, for European Application No. 15154840.1.

* cited by examiner

LIGHT SOURCE DEVICE FOR ENDOSCOPE SYSTEM

CROSS-REFERENCE TO RELATED APPLICATIONS

The present application claims priority under 35 U.S.C. §119 to Japanese Patent Application No. 2014-035959, filed Feb. 26, 2014. The above application is hereby expressly incorporated by reference, in its entirety, into the present application.

BACKGROUND OF THE INVENTION

1. Field of the Invention

The present invention relates to a light source device for an endoscope system.

2. Description Related to the Prior Art

In medical fields, it has become common to perform diagnosis through observing an object of interest (hereinafter simply referred to as the object) in a body cavity with the use of an endoscope system. The endoscope comprises an endoscope, alight source device, and a processor device. The endoscope has an insert section to be inserted into the body cavity. The light source device generates illumination light, which is applied to the object. The processor device obtains an image signal, which is generated by imaging the object through capturing the illumination light reflected from the object, and applies various types of signal processing to the image signal to produce an image of the object.

The endoscope, the light source device, and the processor device are connected to each other through a universal cord extending from a proximal end of the endoscope. The illumination light generated by the light source device is transmitted through a light guide, which extends inside the universal cord and the insertion section, and then applied to the object from a distal end portion of the insert section. The processor device controls an image sensor, which is provided in the distal end portion of the insert section, through electric wiring provided inside the universal cord and the insert section, and obtains the image signal outputted from the image sensor.

In the endoscope system thus configured, the universal cord is easily attached to and detached from the light source device and the processor device, allowing cleaning of the endoscope. Despite the easiness of the connection, the universal cord must be securely connected optically and electrically to the light source device and the processor device. In particular, it is desirable to establish highly precise optical coupling or connection so as to utilize the illumination light efficiently and observe the object with adequate brightness.

There is one type of the light source device which uses a lens to make the illumination light enter the universal cord connected. There is another type of the light source device which incorporates a light guide. The illumination light is transmitted by connecting the universal cord's light guide (hereinafter may referred to as the cord-side light guide) to the incorporated light guide (hereinafter may referred to as the source-side light guide). Among the light source devices which transmit the illumination light by connecting the cord-side light guide to the source-side light guide, there is known a light source device with a mechanism to automatically adjust the position of the source-side light guide at the time of connecting the cord-side light guide to the source-side light guide, so as to establish the highly precise optical coupling or connection (see Japanese Patent No. 5277187 and U.S. Pat. No. 8,517,922 (corresponding to Japanese Patent Laid-Open Publication No. 2006-158859)). Among the light source devices which use the lens to make the illumination light enter the cord-side light guide, there is known a light source device with a mechanism to position the cord-side light guide such that the optical axis of the cord-side light guide is coincident with the optical axis of the lens at the time of connecting the universal cord (see Japanese Patent No. 3089950).

The light guide is flexible, and bending the light guide does not cause loss in the amount of the illumination light. In the case where the light source device transmits the illumination light by connecting the cord-side light guide to the source-side light guide, the illumination light is transmitted to the cord-side light guide with high efficiency by automatically adjusting the position of an end portion of the source-side light guide as described in the Japanese Patent No. 5277187 and the U.S. Pat. No. 8,517,922. However, in the case where the light source device uses the lens to make the illumination light enter the cord-side light guide, a shifting or a displacement in the position of the lens may reduce the incidence efficiency of the illumination light into the cord-side light guide if the lens is moved without care in a manner similar to the positional adjustment of the end portion of the source-side light guide described in the Japanese Patent No. 5277187 and the U.S. Pat. No. 8,517, 922.

In the case of the light source device which uses the lens to make the illumination light enter the cord-side light guide, the position of the lens is fixed and the cord-side light guide is aligned with the lens by inserting the cord-side light guide into an insertion hole which is situated in a specific position relative to the fixed lens as described in the Japanese Patent No. 3089950. Thereby the illumination light is transmitted with high efficiency. However, as compared with the case where the alignment is performed using a movable mechanism as described in the Japanese Patent No. 5277187 and the U.S. Pat. No. 8,517,922, a special care may be needed to connect the universal cord to the light source device depending on positioning accuracy of the cord-side light guide. This may reduce the easiness of the connection. In the case where the cord-side light guide needs to be positioned with extra high accuracy, the end portion of the cord-side light guide may be damaged by careless or rough insertion into the insertion hole.

SUMMARY OF THE INVENTION

An object of the present invention is to provide a light source device, for an endoscope system, which is connected easily to a universal cord and allows illumination light to enter a light guide efficiently in a case where the illumination light enters the light guide through a lens.

A light source device, for an endoscope system, according to the present invention comprises a receiving unit and a movable unit. The light source device for an endoscope system has a light source unit. The light source unit uses a lens to collect light and allow the collected light to enter a light guide provided to an endoscope. The receiving unit receives insertion of the light guide. The receiving unit is attached to the movable unit. The movable unit moves in a direction perpendicular to a direction of the insertion of the light guide in accordance with a force received by the receiving unit from the light guide. The light source unit applies collimated light to the lens attached to the movable unit. The lens moves together with the receiving unit and the movable unit and collects at least a part of the collimated light to the light guide.

It is preferred that the receiving unit has a taper portion for guiding the light guide. The receiving unit, the movable unit, and the lens move in accordance with the force received by the receiving unit from the light guide due to the light guide coming in contact with the taper portion.

It is preferred that the light source device comprises a reference unit, a ball member, and a mounting unit. The reference unit is situated in a predetermined location relative to the collimated light. The movable unit moves with respect to the reference unit. The ball member is rotatably provided between the reference unit and the movable unit. The mounting unit movably attaches the movable unit to the reference unit through the ball member.

It is preferred that the light source device comprises a first bias member for biasing the movable unit toward the reference unit.

It is preferred that the light source device comprises a second bias member for supporting the movable unit relative to the reference unit and biasing a center position of the receiving unit toward a specific position.

It is preferred that the light source device comprises a source-side channel and a flexible connector. The source-side channel is provided to the light source device and connected to an endoscope-side channel provided to the endoscope. The endoscope-side channel protrudes parallel to the light guide. The flexible connector is provided to the source-side channel. The flexible connector is bent, in accordance with a position of insertion of the endoscope-side channel, to receive the insertion of the endoscope-side channel.

It is preferred that the flexible connector is provided in a channel connecting hole. It is preferred that there is a space, between the flexible connector and an inner wall of the channel connecting hole, which allows for bending of the flexible connector.

According to the present invention, there is provided a light source device, for an endoscope system, which is connected easily to a universal cord and allows illumination light to enter a light guide efficiently in the case where the illumination light enters the light guide through a lens.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
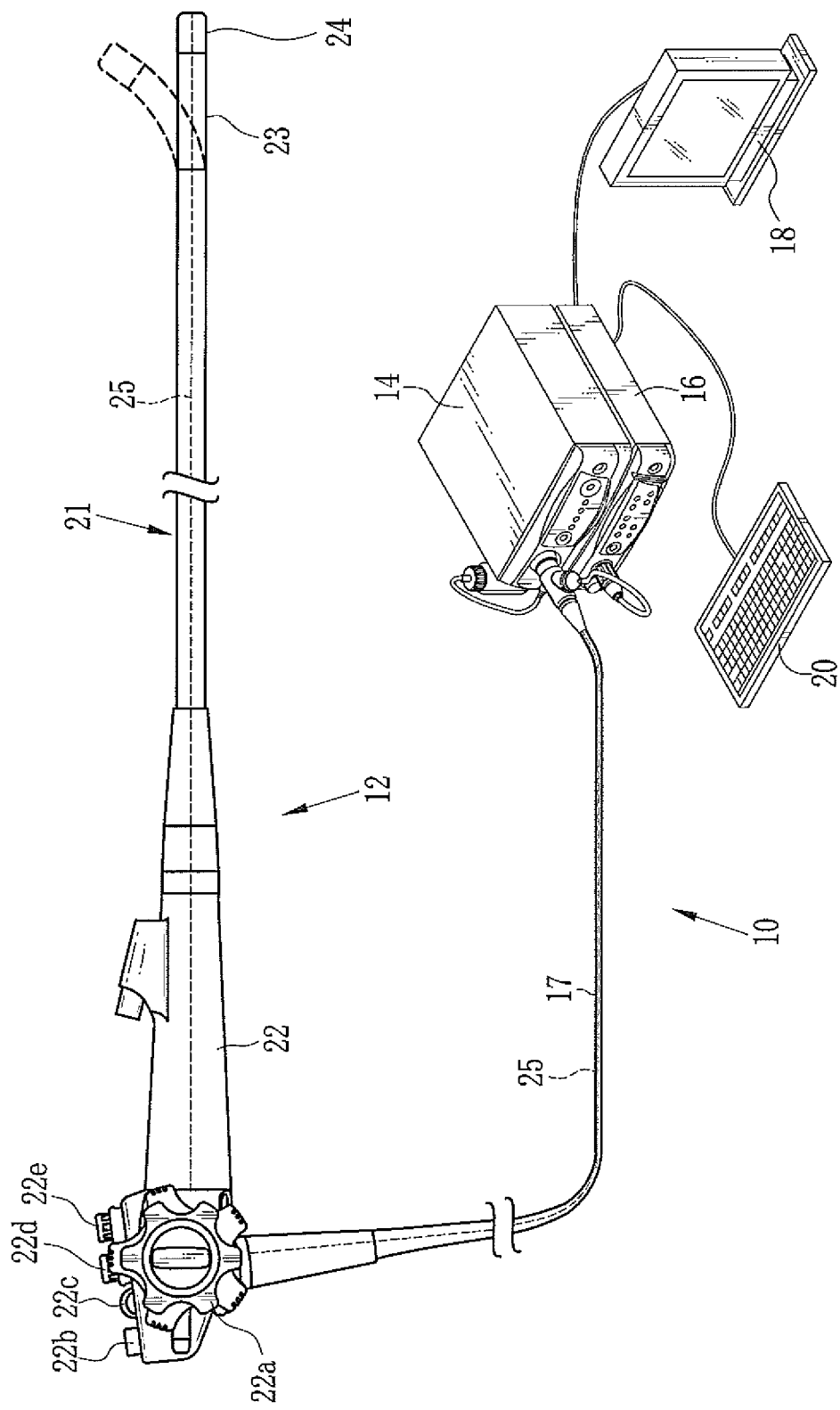
FIG. 1 is an external view of an endoscope system.

As illustrated in FIG. 1, an endoscope system 10 comprises an endoscope 12, a light source device 14, a processor device 16, a monitor 18, and a console 20. The endoscope 12 is connected optically to the light source device 14 and electrically to the processor device 16. The endoscope 12 comprises an insert section 21, which is to be inserted into a body cavity, an operation unit 22, which is provided at a proximal portion of the insert section 21, and a flexible portion 23 and a distal end portion 24, which are provided in a distal portion of the insert section 21. The distal end portion 24 is provided with an illumination optical system, an imaging optical system, an image sensor, and an air/water opening (all not shown). The illumination optical system applies illumination light, which is generated by the light source device 14, to an object of interest (hereinafter simply referred to as the object). The imaging optical system and the image sensor are used for imaging the object through capturing the illumination light reflected from the object. The air/water opening applies (or ejects) air and water to the body cavity. The flexible portion 23 is bent as desired by operating an angle knob 22a of the operation unit 22. The flexible portion 23 is bent to direct the distal end portion 24 to a desired direction. The operation unit 22 is further provided with a freeze button 22b operated for storing a still image, a zoom operation unit 22c operated for zooming of the imaging optical system, an air/water button 22d operated to eject water or air through the air/water opening, a suction button 22e operated to suck contents or the like from the body cavity, and the like.

The light source device 14 generates the illumination light to be applied to the object. The illumination light is, for example, white light or narrowband light having a specific wavelength range. The illumination light is switched depending on a purpose of the observation or diagnosis. The light source device 14 is connected to the processor device 16. Based on a control signal inputted from the processor device 16, the light source device 14 adjusts the light amount, the wavelength range, the emission timing, and the like of the illumination light.

The processor device 16 is connected electrically to the endoscope 12, the light source device 14, the monitor 18, and the console 20. The processor device 16 controls imaging of the image sensor. The processor device 16 obtains an image signal outputted from the image sensor, produces an image of the object, and allows the monitor 18 to display the image. The console 20 functions as a UI (user interface) that accepts input operation such as setting a function.

The endoscope 12, the light source device 14, and the processor device 16 are connected to each other by a universal cord 17 that extends from a proximal end portion of the endoscope 12. The universal cord 17 is provided with a light guide 25 that transmits the illumination light generated by the light source device 14. The illumination light is incident on the light guide 25 by connecting the universal cord 17 to the light source device 14. The light guide 25 extends from the universal cord 17 to the distal end portion 24 through the inside of the insert section 21. The light guide 25 transmits the illumination light, which is incident from the light source device 14, to the distal end portion 24. The transmitted illumination light is applied to the object through the illumination optical system. Inside the universal cord 17, there are an air/water channel (not shown), which feeds air or water, and wiring (not shown) electrically connected to the image sensor and the like. The air/water channel is connected to an air pump 39a (see FIG. 2) provided in the light source device 14. The wiring is also connected to the processor device 16.

Figure 2:
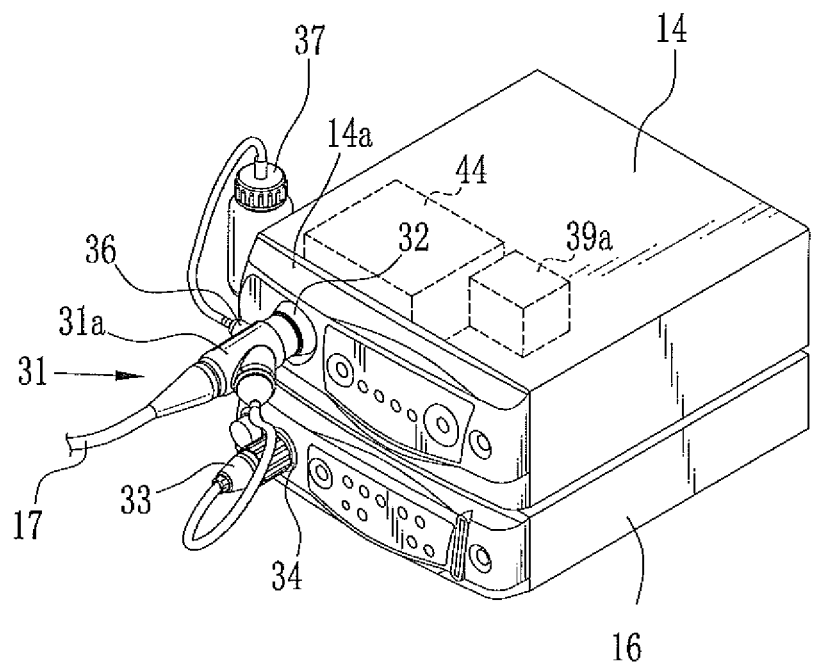
FIG. 2 is a perspective view illustrating a connection part between a universal cord and a light source device.

As illustrated in FIG. 2, a connector (hereinafter referred to as the cord-side optical connector) 31, which is used for connection to the light source device 14, is provided at an end of the universal cord 17. The cord-side optical connector 31 is fitted into a connector (hereinafter referred to as the source-side optical connector) 32 provided on the light source device 14. Thereby the endoscope 12 is optically connected to the light source device 14. To be more specific, a light source unit 44 is disposed behind the source-side optical connector 32. The light source unit 44 is composed of LEDs (light emitting diodes) and the like, which generate the illumination light. By connecting the cord-side optical connector 31 to the source-side optical connector 32, the illumination light from the light source unit 44 is able to enter the light guide 25. The illumination light generated by the light source unit 44 is collimated (parallel) light. The air/water channel is connected to the cord-side optical connector 31. By connecting the cord-side optical connector 31 to the source-side optical connector 32, the air/water channel is connected to the air pump 39a.

A connector (hereinafter referred to as the cord-side electrical connector) 33, which is used for connection to the processor device 16, branches off from a body 31a of the cord-side optical connector 31. The cord-side electrical connector 33 is provided with a contact connected to the wiring inside the universal cord 17. By connecting the cord-side electrical connector 33 to a connector (hereinafter referred to as the processor-side electrical connector) 34 of the processor device 16, electronic parts such as the image sensor in the endoscope 12 are able to communicate control signals and image signals with the processor device 16. A water feed ring 36, which is connected to the air/water channel, is provided on the body 31a of the cord-side optical connector 31. A water tank 37 is connected to the water feed ring 36.

Figure 3:
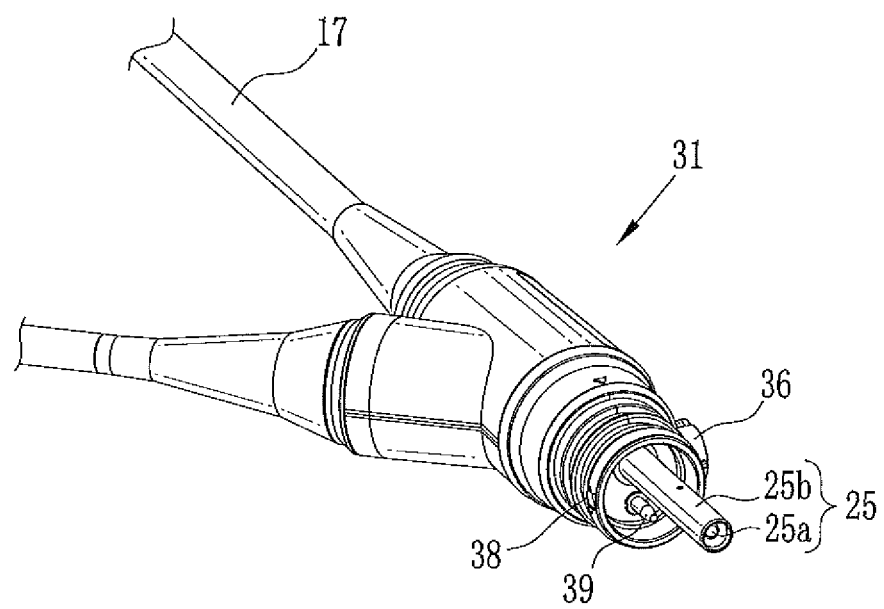
FIG. 3 is a perspective view of a cord-side optical connector.

As illustrated in FIG. 3, the light guide 25 and an air nozzle 39 protrude from the inside of an end ring 38 provided at an end face of the cord-side optical connector 31. The end ring 38 fits into the source-side optical connector 32. The light guide 25 at an end portion (including the end face) of the cord-side optical connector 31 is composed of an optical fiber bundle 25a, being optical fibers tied together, and a sheath 25b that covers the optical fiber bundle 25a. There are cases where the optical fiber bundle 25a is referred to as a light guide and the optical fiber bundle 25a covered with the sheath 25b is referred to as a light guide rod, but in this embodiment, the optical fiber bundle 25a covered with the sheath 25b is referred to as the light guide 25. The air nozzle 39 is a channel inside the endoscope 12 and connected to the air/water channel.

Figure 4:
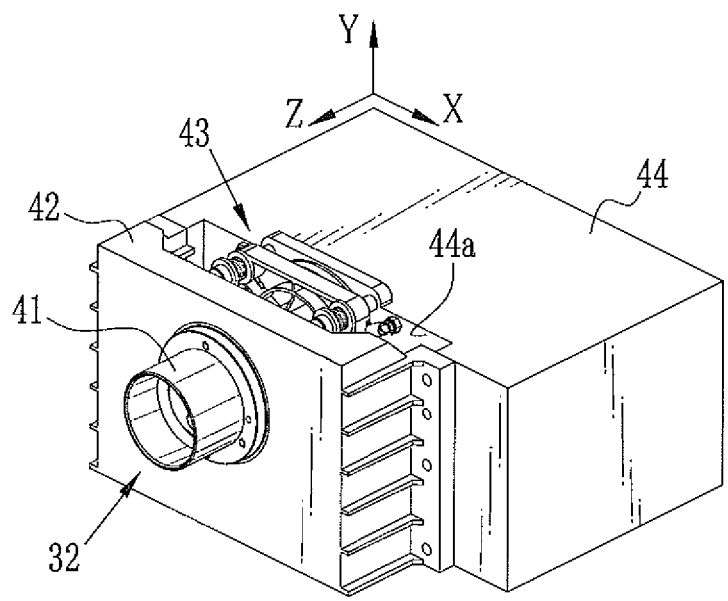
FIG. 4 is a perspective view of a source-side optical connector.
Figure 5:
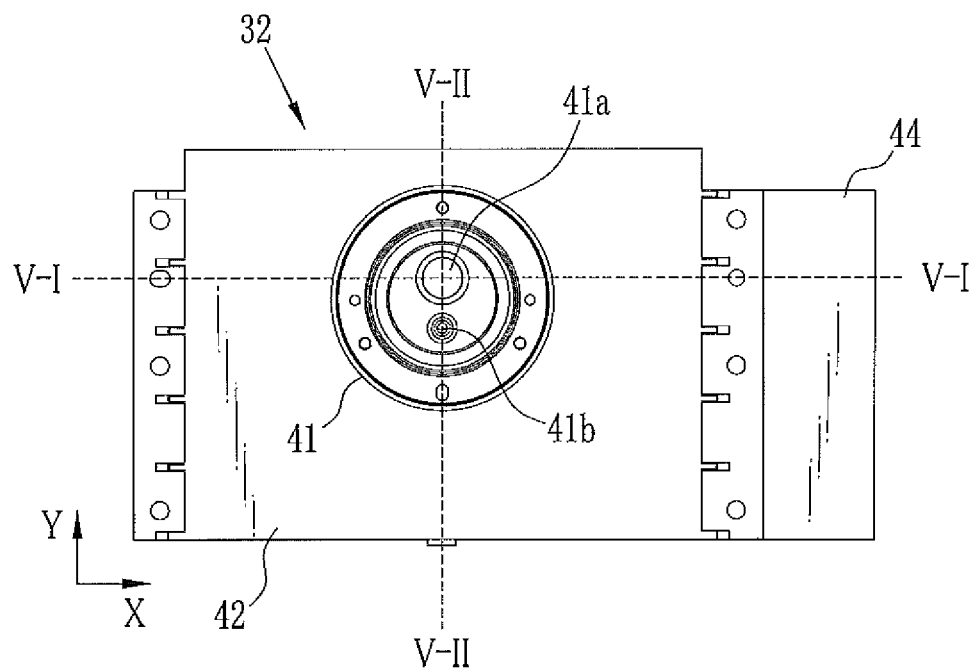
FIG. 5 is a front view of the source-side optical connector.

As illustrated in FIG. 4, the source-side optical connector 32 comprises a fitting 41, a fitting mount 42, and a follow mechanism 43. The fitting 41 is exposed from a decorative panel 14a (see FIG. 2) of the light source device 14. The fitting 41 and the end ring 38 of the cord-side optical connector 31 fit together. As illustrated in FIG. 5, a light guide insertion opening 41a and an air nozzle insertion opening 41b are provided inside the fitting 41. When the cord-side optical connector 31 is connected to the source-side optical connector 32, the light guide 25 is inserted into the light guide insertion opening 41a and the air nozzle 39 is inserted into the air nozzle insertion opening 41b.

The fitting mount 42 and the follow mechanism 43 are provided behind the decorative panel 14a. The fitting mount 42 is a base on which the fitting 41 is provided. The fitting mount 42 is attached to the light source unit 44 composed of the LEDs and the like, which generate the illumination light. The fitting mount 42 has a shape with the front face, on which the fitting 41 is provided, protruded relative to the light source unit 44. Owing to the shape of the fitting mount 42, a space is provided between the fitting mount 42 and the light source unit 44. The follow mechanism 43 is disposed inside the space.

The follow mechanism 43 is provided to a front portion 44a of the light source unit 44. The front portion 44a is situated in a predetermined location relative to the collimated illumination light from the light source unit 44. The front portion 44a functions as a reference (reference unit) with respect to which the movable follow mechanism 43 moves. A lens 50 (see FIG. 6, the lenses 50 may be referred to as the lens 50), which makes the illumination light enter the light guide 25 inserted in the light guide insertion opening 41a, is attached to the follow mechanism 43. The follow mechanism 43 is capable of moving in a direction (XY in-plane direction) within an XY plane perpendicular to an insertion direction (Z direction), in which the light guide 25 is inserted. The follow mechanism 43 comes in contact with the light guide 25 and is moved in accordance with a force exerted by the light guide 25. To be more specific, the follow mechanism 43 receives the insertion of the light guide 25 and comes in contact with the light guide 25 when the cord-side optical connector 31 is connected to the source-side optical connector 32. The follow mechanism 43 follows the motion of the light guide 25 caused by the contact with the follow mechanism 43 and slides the lens 50 in the direction of the force exerted by the light guide 25.

Figure 6:
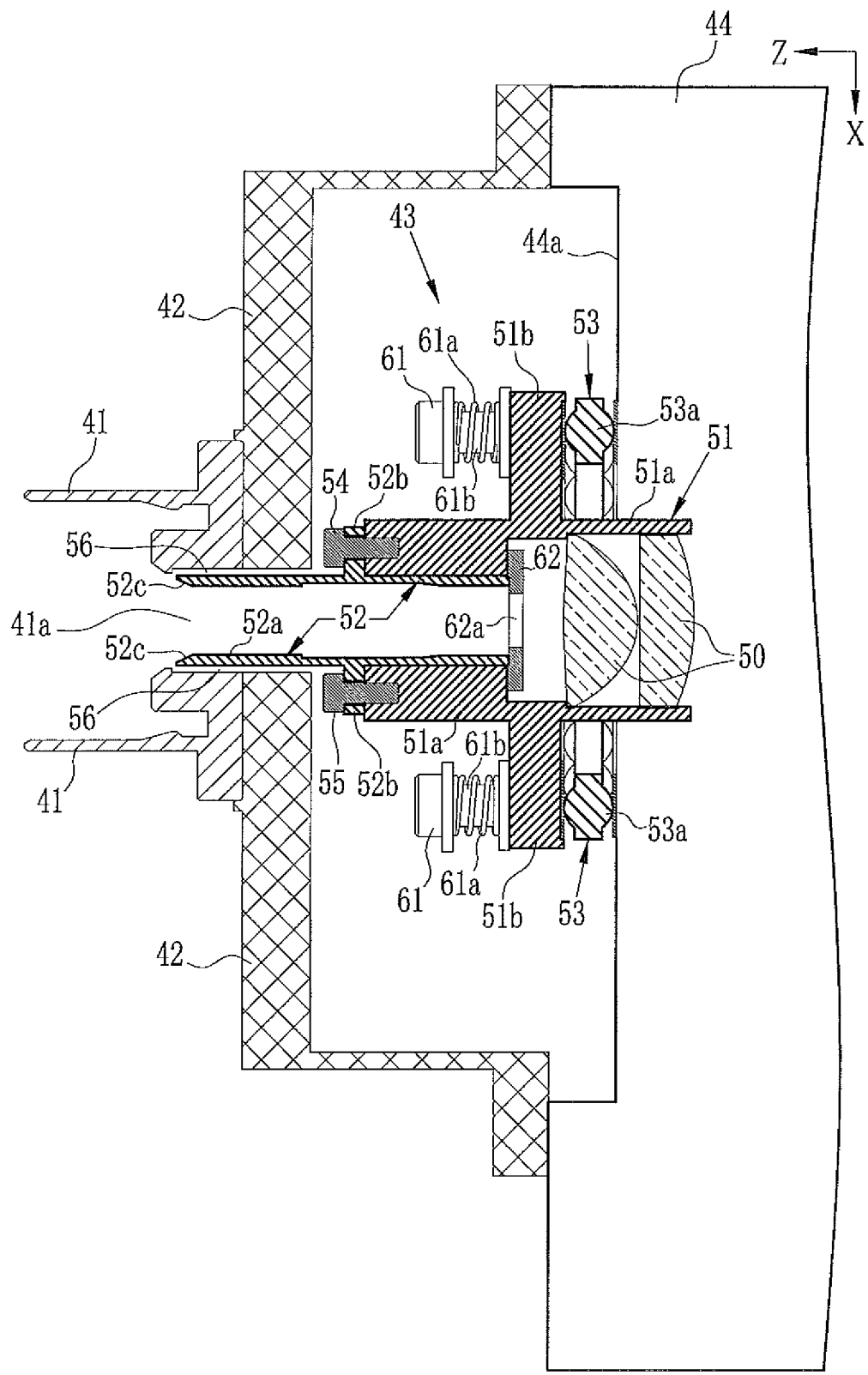
FIG. 6 is a cross-sectional view of the source-side optical connector across a line V-I.

As illustrated in FIG. 6, the follow mechanism 43 comprises a lens barrel 51, a receiving unit 52, and ball members 53. The lens barrel 51 comprises a cylindrical body 51a and a flange 51b extending from the body 51a in a direction perpendicular to the insertion direction of the light guide 25. The flange 51b is provided in the approximate middle of the body 51a in the longitudinal direction. The lens barrel 51 holds the lens 50 inside a portion of the body 51a on the light source unit 44 side relative to the flange 51b.

The lens barrel 51 is attached to the front portion 44a by mounting units 61 through the respective ball members 53 each located between the flange 51b and the front portion 44a of the light source unit 44. The ball member 53 rotatably holds a ball 53a at a position illustrated in the drawing. The mounting unit 61 fixes the lens barrel 51 to the front portion 44a with a mounting pin 61b while biasing the lens barrel 51 in a direction to press the lens barrel 51 against the light source unit 44 with the use of a spring 61a (first bias member). Thereby the motion of the lens barrel 51 in the Z direction is limited. Note that the flange 51b is provided with a through hole (not shown), through which the mounting pin 61b is inserted. The diameter of the through hole is greater than that of the mounting pin 61b, so that a certain play or clearance is left. The bias force of the spring 61a is at a level only to maintain the contact between the flange 51b and the ball member 53 and the contact between the ball member 53 and the front portion 44a, and allows the lens barrel 51 to move within the XY plane. The lens barrel 51 moves freely in the XY in-plane direction within a range of the play between the mounting pin 61b and the through hole, through which the mounting pin 61b is inserted.

The receiving unit 52 is attached to an end portion of the body 51a on the fitting 41 side. The receiving unit 52 comprises a cylindrical casing 52a and a flange 52b that extends, from the casing 52a, in a direction perpendicular to the insertion direction of the light guide 25. The inner diameter of the cylindrical casing 52a is substantially the same as the diameter of the light guide 25. An end portion of the receiving unit 52 extending from the flange 52b to the light source unit 44 side is inserted in the body 51a of the lens barrel 51. The flange 52b is fastened with screws 54 and 55 and the like to the body 51a of the lens barrel 51. An end portion of the casing 52a on the fitting 41 side extends from the inside of the body 51a of the lens barrel 51 and protrudes toward the light guide insertion opening 41a. A stop member 62 is provided at the other end portion of the casing 52a and inside the body 51a of the lens barrel 51. A center portion 62a of the stop member 62 is an opening through which the illumination light passes. An edge of the stop member 62 protrudes toward the center of the receiving unit 52. When the cord-side optical connector 31 is connected to the source-side optical connector 32, a leading end of the light guide 25 inserted into the receiving unit 52 abuts against the stop member 62. Note that the opening in the center portion 62a is unnecessary in a case where the stop member 62 is made from a transparent material.

A taper portion 52c for guiding the light guide 25 into the receiving unit 52 is formed on an inner surface of the end portion of the casing 52a on the fitting 41 side. From the light guide 25 being inserted and coming in contact with the taper portion 52c, the receiving unit 52 and the lens barrel 51, to which the receiving unit 52 is fastened, receive the force which contains a component in the direction perpendicular to the insertion direction of the light guide 25. The force caused by the light guide 25 coming in contact with the taper portion 52c moves the follow mechanism 43. In other words, in this embodiment, the lens barrel 51 is a movable unit that moves in the direction perpendicular to the insertion direction of the light guide 25, in accordance with the force received from or exerted by the light guide 25. Note that there is a clearance or space 56, which allows for the motion or displacement of the receiving unit 52, between the receiving unit 52 and the fitting 41 and the fitting mount 42.

Figure 7:
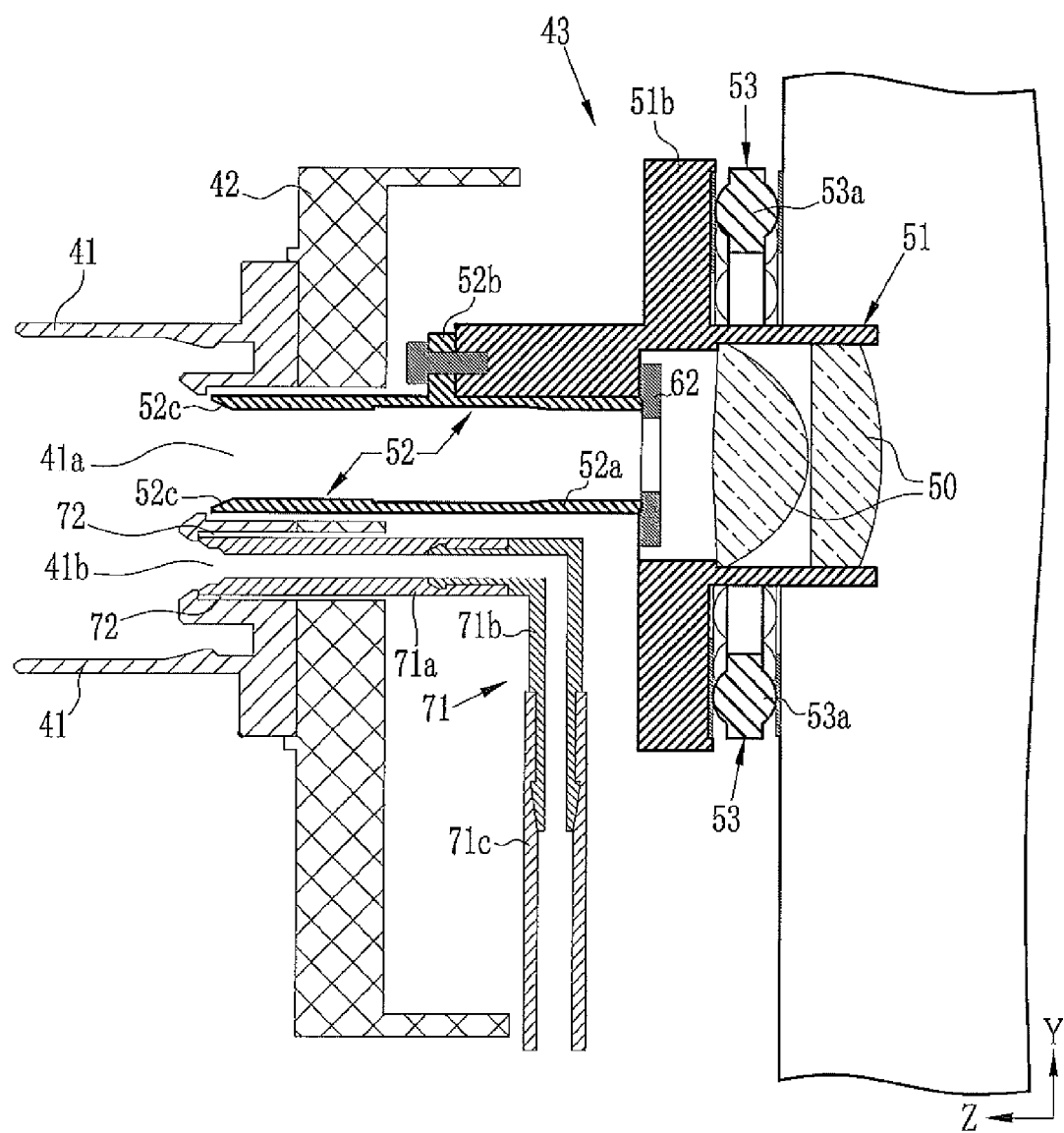
FIG. 7 is a cross-sectional view of the source-side optical connector across a line V-II.

As illustrated in FIG. 7, an air tube 71 (source-side channel), to which the air nozzle 39 is to be connected or inserted, is provided inside and behind the air nozzle insertion opening 41b. The air tube 71 comprises a first flexible connector 71a, which is placed inside and immediately behind the air nozzle insertion opening 41b, a bent tube 71b, which is bent in an L shape on the fitting 41 side that is forward of the lens barrel 51, and a second flexible connector 71c that connects the bent tube 71b and the air pump 39a. The first flexible connector 71a and the second flexible connector 71c are formed from, for example, silicone rubber, and bent freely. The first flexible connector 71a is disposed inside a hole (hereinafter referred to as the channel connecting hole) formed through the fitting 41 and the fitting mount 42. There is a clearance or space 72, which allows for bending of the first flexible connector 71a, between the first flexible connector 71a and an inner wall of the channel connecting hole. When the air nozzle 39 is inserted into the air nozzle insertion opening 41b, the first flexible connector 71a bends in accordance with the insertion position of the air nozzle 39. Thereby the air nozzle 39 is securely connected to the air tube 71 even if the center axes of the air nozzle 39 and the air nozzle insertion opening 41b are shifted from each other.

Figure 8:
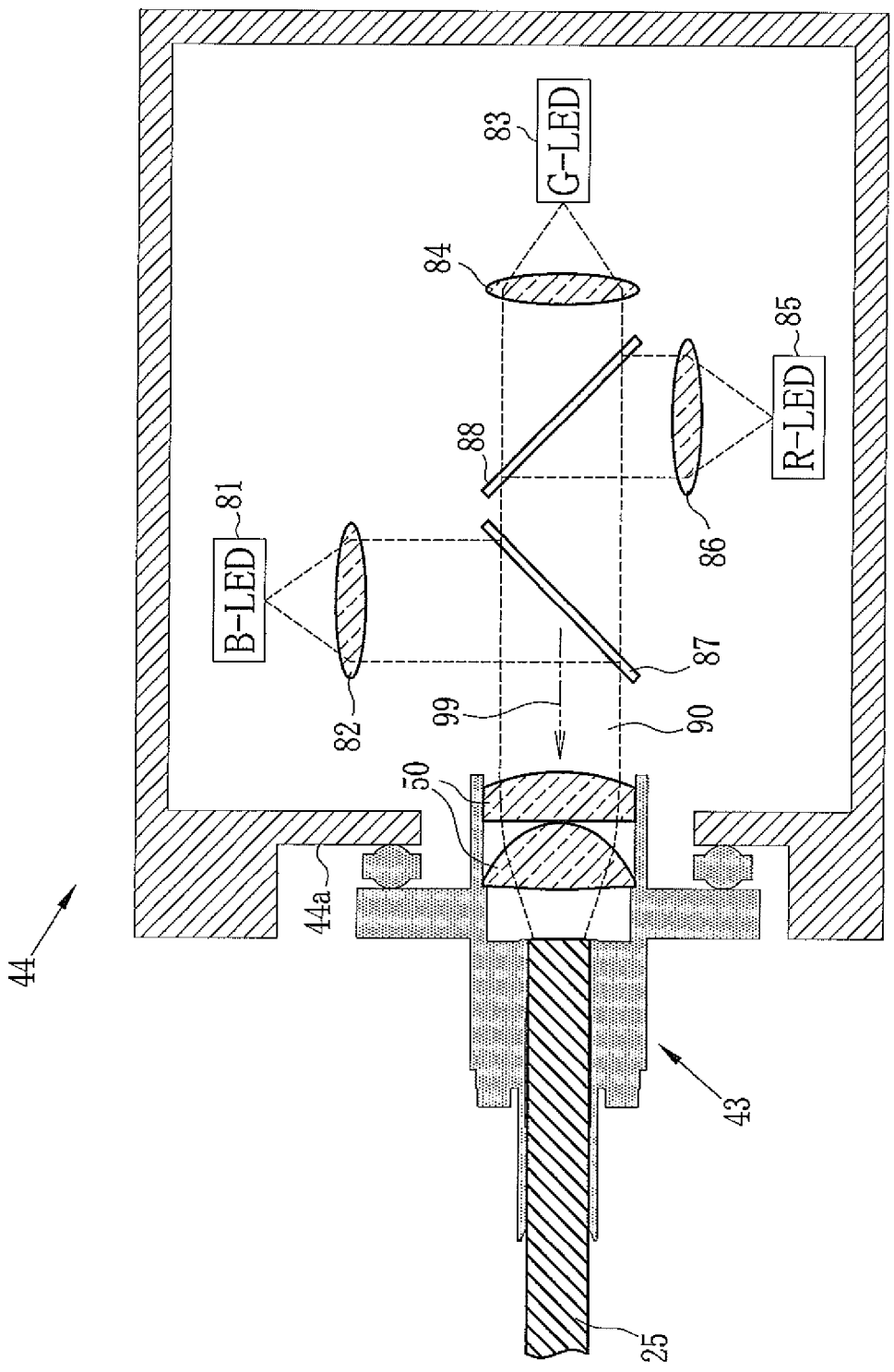
FIG. 8 is an explanatory view of a light source unit.

As illustrated in FIG. 8, the light source unit 44 comprises, for example, an LED (hereinafter referred to as the B-LED) 81 that emits blue light, a collimator lens 82 that converts the blue light from the B-LED 81 into collimated light, an LED (hereinafter referred to as the G-LED) 83 that emits green light, a collimator lens 84 that converts the green light from the G-LED 83 into collimated light, an LED (hereinafter referred to as the R-LED) 85 that emits red light, and a collimator lens 86 that converts the red light from the R-LED 85 into collimated light.

The light source unit 44 also comprises a dichroic mirror 87, which reflects the blue light and passes the green light and the red light, and a dichroic mirror 88, which reflects the red light and passes the green light. The blue light from the B-LED 81 is converted into the collimated light by the collimator lens 82, and then reflected by the dichroic mirror 87. Thereby the blue light (the collimated light) is transmitted to the lens 50 that is held by the follow mechanism 43. The green light from the G-LED 83 is converted into the collimated light by the collimator lens 84, and then passes through the dichroic mirrors 87 and 88. The green light (the collimated light) is transmitted to the lens 50 that is held by the follow mechanism 43. In a like manner, the red light from the R-LED 85 is converted into the collimated light by the collimator lens 86, and reflected by the dichroic mirror 88, and then passes through the dichroic mirror 87. Thereby the red light (the collimated light) is transmitted to the lens 50 that is held by the follow mechanism 43. Thus, in the case where the B-LED 81, the G-LED 83, and the R-LED 85 are turned on at the same time, the light source unit 44 transmits white collimated light (illumination light 90) to the lens 50 that is held by the follow mechanism 43. The light source unit 44 changes the spectrum of the illumination light 90 through turning on or off the B-LED 81, the G-LED 83, and/or the R-LED 85 or adjusting (or changing) the amount of light from each of the LEDs 81, 83, and 85. In any case, the illumination light 90 transmitted to the lens 50 is collimated or parallel. Note that, throughout the specification, the "collimated light" may not be precisely collimated (parallel) and includes substantially parallel light.

Figure 9:
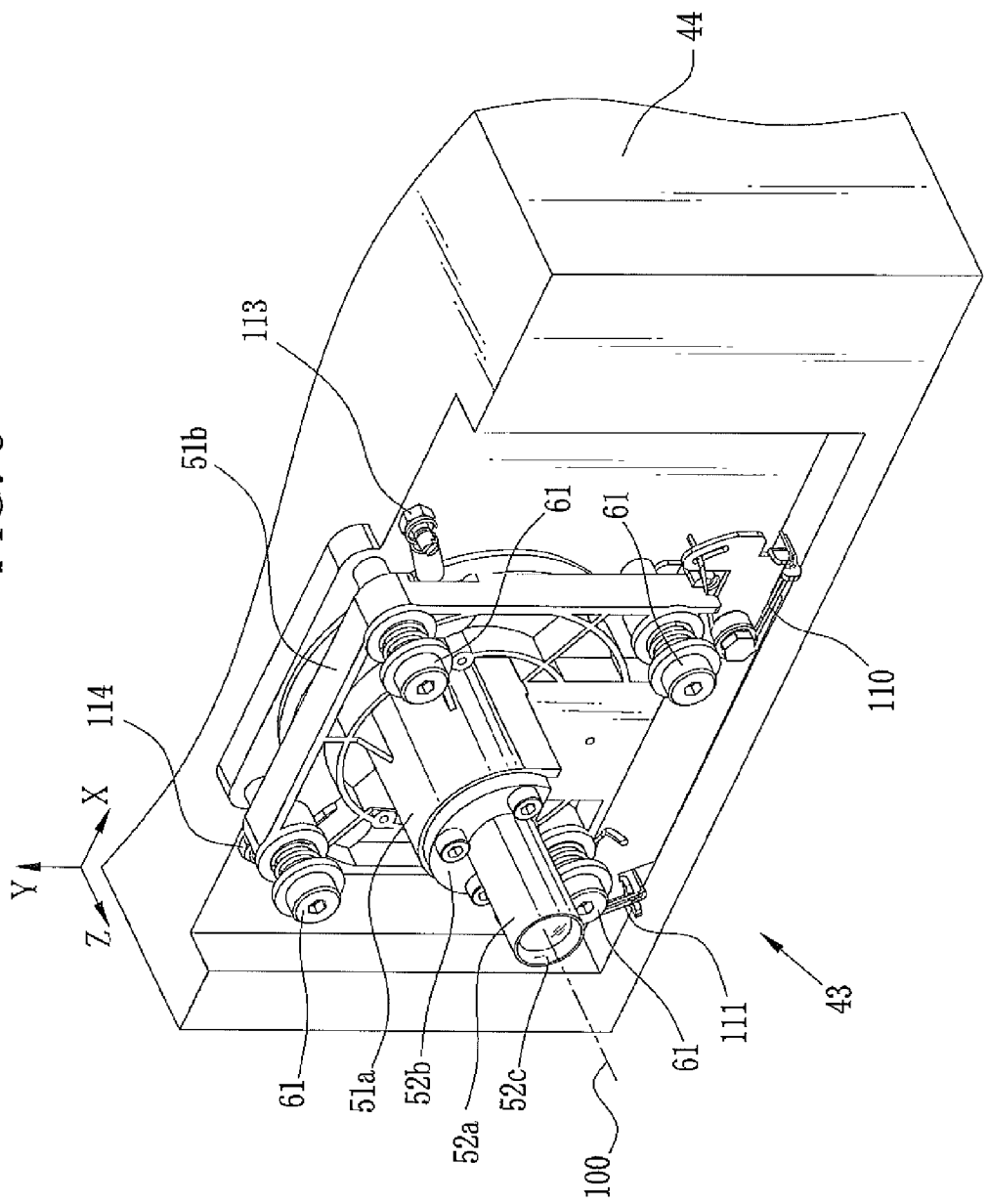
FIG. 9 is a perspective view illustrating the source-side optical connector with a fitting mount removed.
Figure 10:
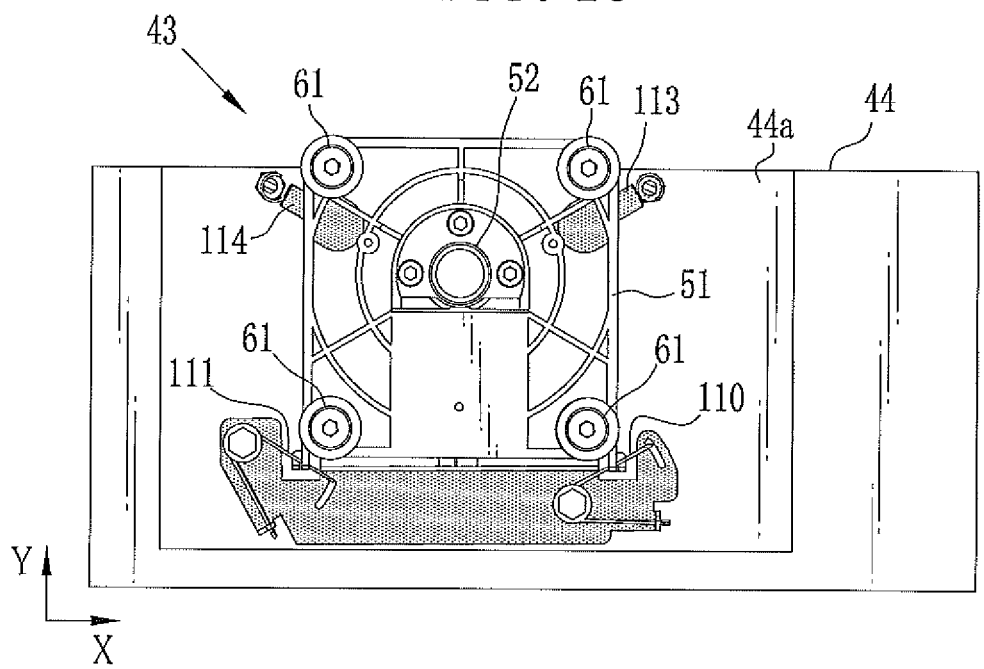
FIG. 10 is a front view of the source-side optical connector with the fitting mount removed.

As illustrated in FIGS. 9 and 10, the follow mechanism 43 comprises bias members (second bias members) 110, 111, 113, and 114, which bias and support the lens barrel 51. The bias members 110 and 111 bias the lens barrel 51 at the two vertical lower corners of the lens barrel 51. The bias members 113 and 114 bias the lens barrel 51 in directions to substantially pull up the lens barrel 51. The bias force of each of the bias members 110, 111, 113, and 114 is balanced with gravity acting on the lens barrel 51 and the receiving unit 52 when the light guide 25 is not inserted into the receiving unit 52. Thus the bias members 110, 111, 113, and 114 keep the position of a center axis (that is, the optical axis of the lens 50) 100, against the gravity, to be coincident with a center 99 (see FIG. 8) of the illumination light 90.

Figure 11:
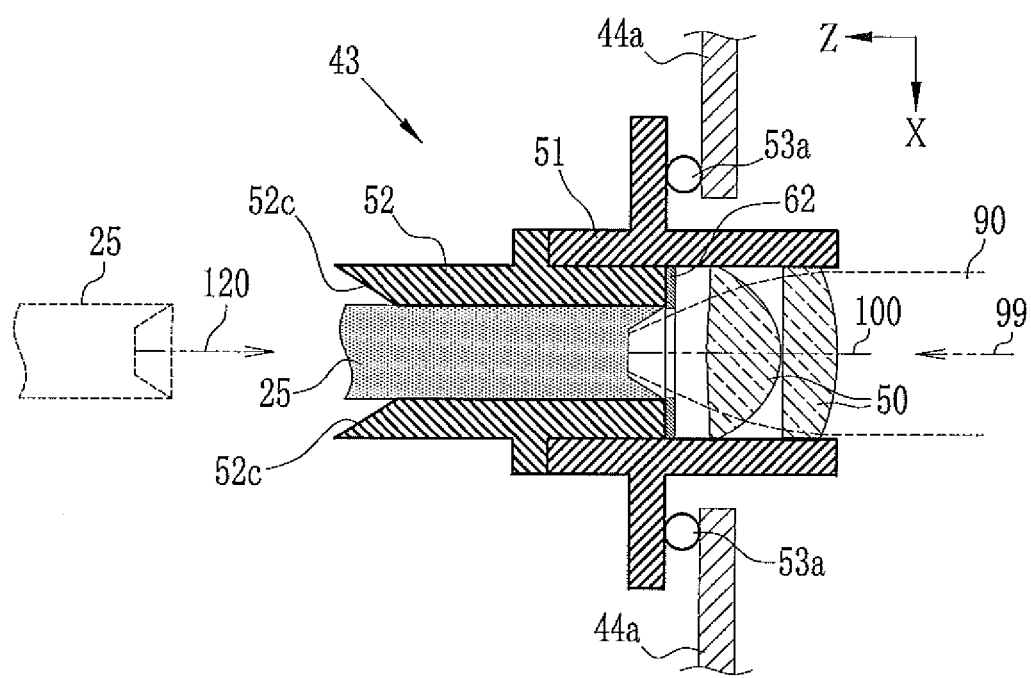
FIG. 11 is an explanatory view illustrating an operation of the light guide connected with its center axis coincident with the center of illumination light.

Hereinafter, operations of the light source device 14 and the source-side optical connector 32 of the above-described configurations are described. First, as illustrated in FIG. 11, before connecting the cord-side optical connector 31 to the source-side optical connector 32, the position of the center axis (the optical axis of the lens 50) 100 is kept coincident with the center 99 of the illumination light 90. In the case where the cord-side optical connector 31 is connected to the source-side optical connector 32 with a center axis 120 of the light guide 25 coincident with the center 99 of the illumination light 90, the light guide 25 is inserted into the receiving unit 52 without coming in contact with the taper portion 52c. Then the leading end of the light guide 25 abuts against the stop member 62. In this state, the illumination light 90 enters the light guide 25 most efficiently.

Figure 12:
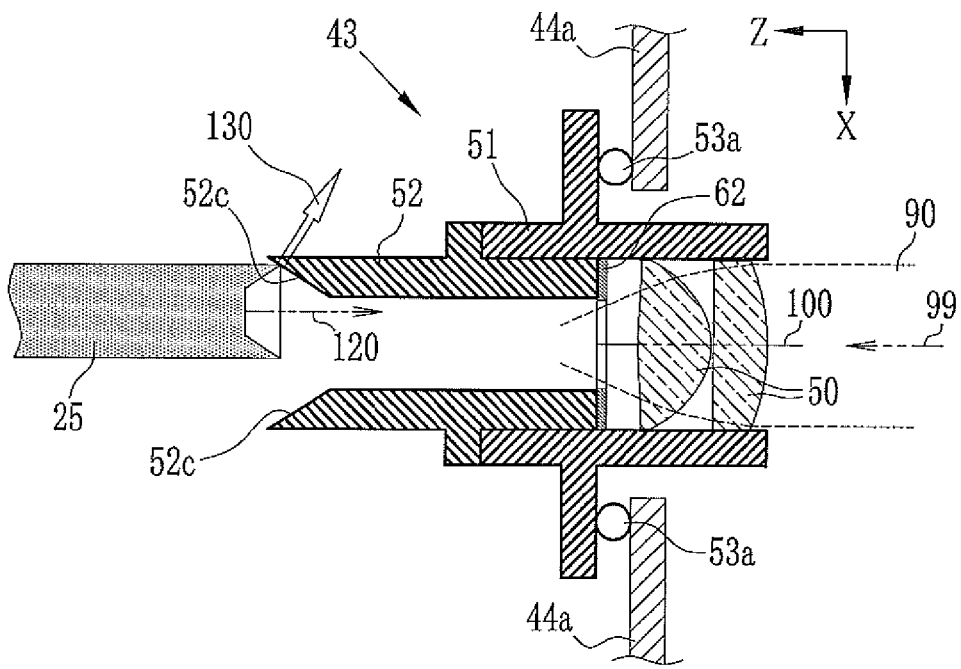
FIG. 12 is an explanatory view illustrating an operation of the light guide connected with its center axis slightly shifted from the center of illumination light.
Figure 13:
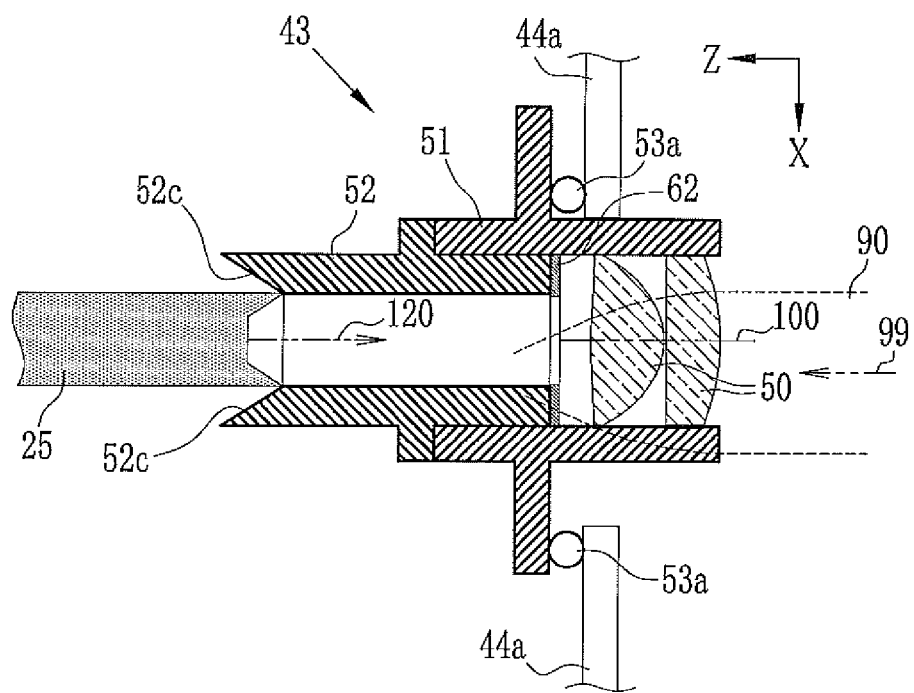
FIG. 13 is an explanatory view illustrating an operation of the light guide connected with its center axis slightly shifted from the center of illumination light.

As illustrated in FIG. 12, in a case where the cord-side optical connector 31 is connected to the source-side optical connector 32 with the center axis 120 of the light guide 25 shifted from the center 99 of the illumination light 90, the leading end of the light guide 25 comes in contact with the taper portion 52c of the receiving unit 52. When the leading end of the light guide 25 comes in contact with the taper portion 52c of the receiving unit 52, the receiving unit 52 receives a force indicated by an arrow 130 from the pressing light guide 25. The receiving unit 52 and the lens barrel 51, to which the receiving unit 52 is attached, move smoothly in the XY in-plane direction along the front portion 44a of the light source unit 44 as the ball 53a is rotated. As illustrated in FIG. 13, the receiving unit 52 and the lens barrel 51 slide in accordance with a component (that is, the component in the XY in-plane direction) of the force acting in the direction of the arrow 130. Thereby, the light guide 25 is guided or introduced into the receiving unit 52. Thus, the light guide 25 is smoothly inserted into the receiving unit 52 by pushing the cord-side optical connector 31 into the source-side optical connector 32 even if the center axis 120 of the light guide 25 is shifted from the center 99 of the illumination light 90.

Figure 14:
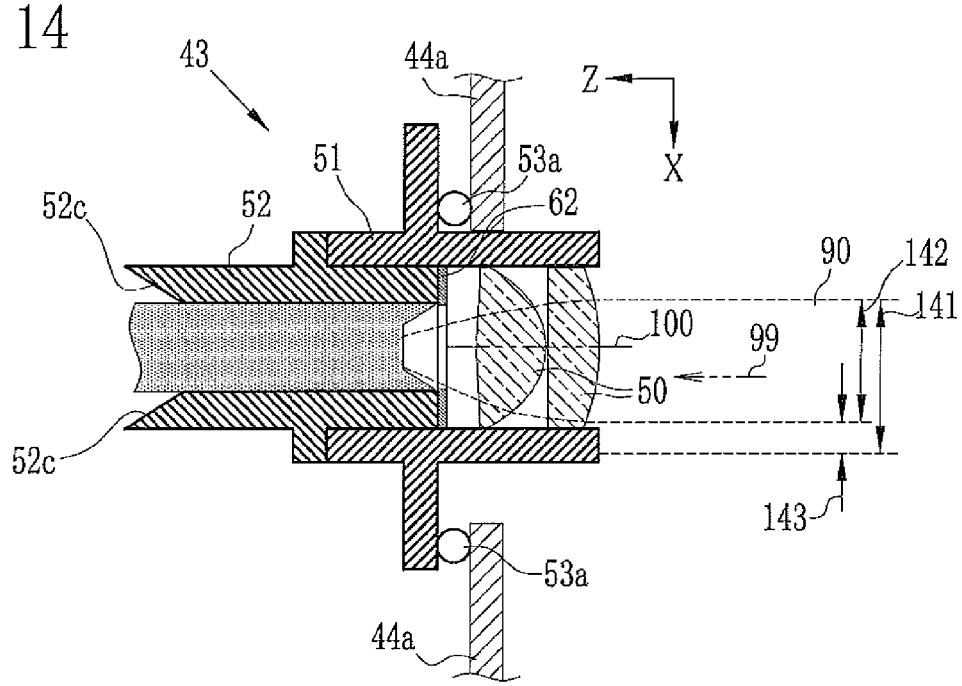
FIG. 14 is an explanatory view illustrating an operation of the light guide connected with its center axis slightly shifted from the center of illumination light.

Thereafter, as illustrated in FIG. 14, the connection between the cord-side optical connector 31 and the source-side optical connector 32 is completed when the leading end of the light guide 25 abuts against the stop member 62. At this time, the position from which the illumination light 90 is applied to the lens 50 is not changed, but the positions of the lens 50 and the lens barrel 51 are slightly shifted together. Thereby, of all the light beams (or light flux) of the illumination light 90 in an area indicated by an arrow 141, the light beams (or light flux) in an area indicated by an arrow 142 enter the light guide 25, but the light beams (or light flux) in an area indicated by arrows 143 do not enter the light guide 25. As a result, partial loss of the illumination light 90 occurs. However, since the illumination light 90 is the collimated light and the lens 50 slides (or shifts) only in the direction perpendicular to the center 99 of the collimated light, the loss of the illumination light is suppressed to a minimum level as compared with a case where the illumination light 90 is not the collimated light (for example, a case where the light beams converge).

As described above, with the use of the light source device 14 and the source-side optical connector 32 provided with the follow mechanism 43, the light guide 25 is smoothly guided or introduced into the receiving unit 52 even if the insertion position of the light guide 25 is slightly shifted. Thus, the cord-side optical connector 31 is easily connected to the source-side optical connector 32 without extra care. Furthermore, the illumination light 90 is collimated and the lens 50 that allows the collimated illumination light 90 to enter the light guide 25 is moved. Moving the lens 50 by use of the follow mechanism 43 suppresses loss in the amount of light entering the light guide 25 to a minimum. Thereby the lens 50 allows approximately the entire amount of the illumination light 90 to enter the light guide 25.

Even if a xenon lamp is used to generate the illumination light as described in Japanese Patent No. 3089950, highly precise optical coupling or connection is required between the universal cord and the light source device. Since the light emission point and the light flux of the LED are smaller than those of the xenon lamp, the light source device 14 which uses the LED to generate the illumination light requires the connection with higher precision than that of the device using the xenon lamp. According to the present invention, the collimated illumination light 90 is used and the lens 50 that allows the illumination light 90 to enter the light guide 25 is retained by the follow mechanism 43 as described in the above embodiment. Thereby the loss in the light amount is suppressed to a minimum even if the LED is used to generate the illumination light 90, and the illumination light 90 is transmitted to the light guide 25 efficiently. Thus the present invention is especially suitable for the light source device which uses the LED to generate the illumination light.

Note that it is preferred that the follow mechanism 43 moves the lens 50 within a range to make a ratio of the amount of the illumination light 90 incident on the light guide 25 to the total amount of the illumination light 90 to be greater than or equal to 0.99 and less than or equal to 1.00. In other words, the loss in the amount of the illumination light 90 is preferred to be less than or equal to 1% in the case where the lens 50 is slid by the follow mechanism 43 that follows (or is moved by) the insertion of the light guide 25. The total amount of light refers to the sum of the amounts of the light beams at all points in a certain area (for example, the area indicated by the arrow 141 in FIG. 14) in the direction toward the lens 50. The amount of light incident on the light guide 25 refers to the amount of light actually entering the light guide 25, for example, the sum of the amounts of the light beams at all points in the area indicated by the arrow 142 in FIG. 14.

Figure 15:
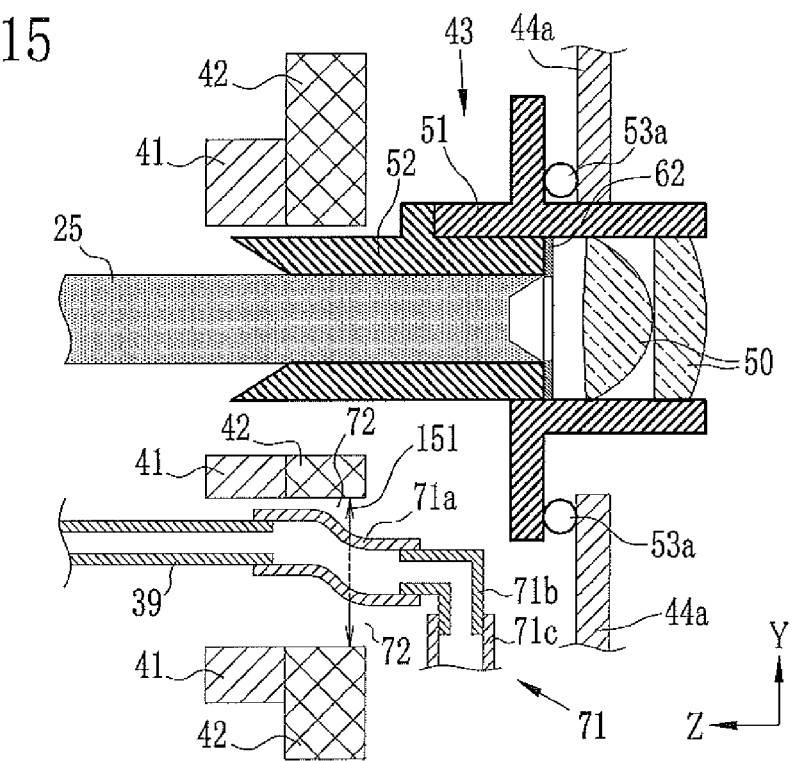
FIG. 15 is a cross-sectional view illustrating connection to an air nozzle.

Since the distance between the light guide 25 and the air nozzle 39 is constant, the insertion position of the air nozzle 39 into a channel connecting hole 151 is shifted when the follow mechanism 43 slides to align with the insertion position of the light guide 25 as illustrated in FIG. 15. As for the light source device 14 and the source-side optical connector 32, the first flexible connector 71a is disposed in the channel connecting hole 151, and the space 72 is provided between an inner wall of the channel connecting hole 151 and the first flexible connector 71a. The space 72 allows for bending of the first flexible connector 71a. The connection between the air nozzle 39 and the air tube 71 is ensured by allowing the first flexible connector 71a to bend even if the insertion position of the air nozzle 39 into the channel connecting hole 151 is slightly shifted.

(Second Embodiment)

Figure 16:
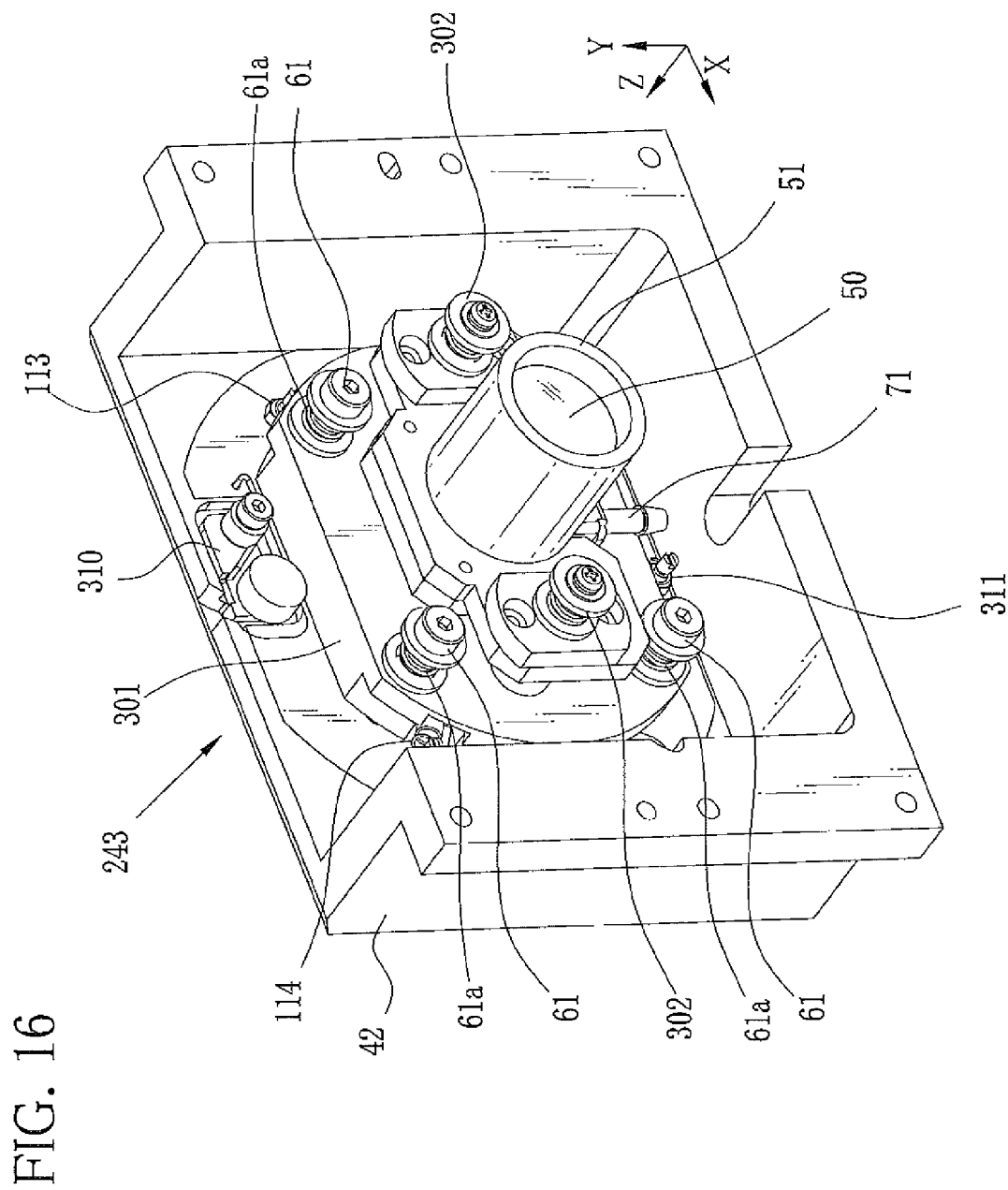
FIG. 16 is a perspective view illustrating a follow mechanism according to a second embodiment.
Figure 17:
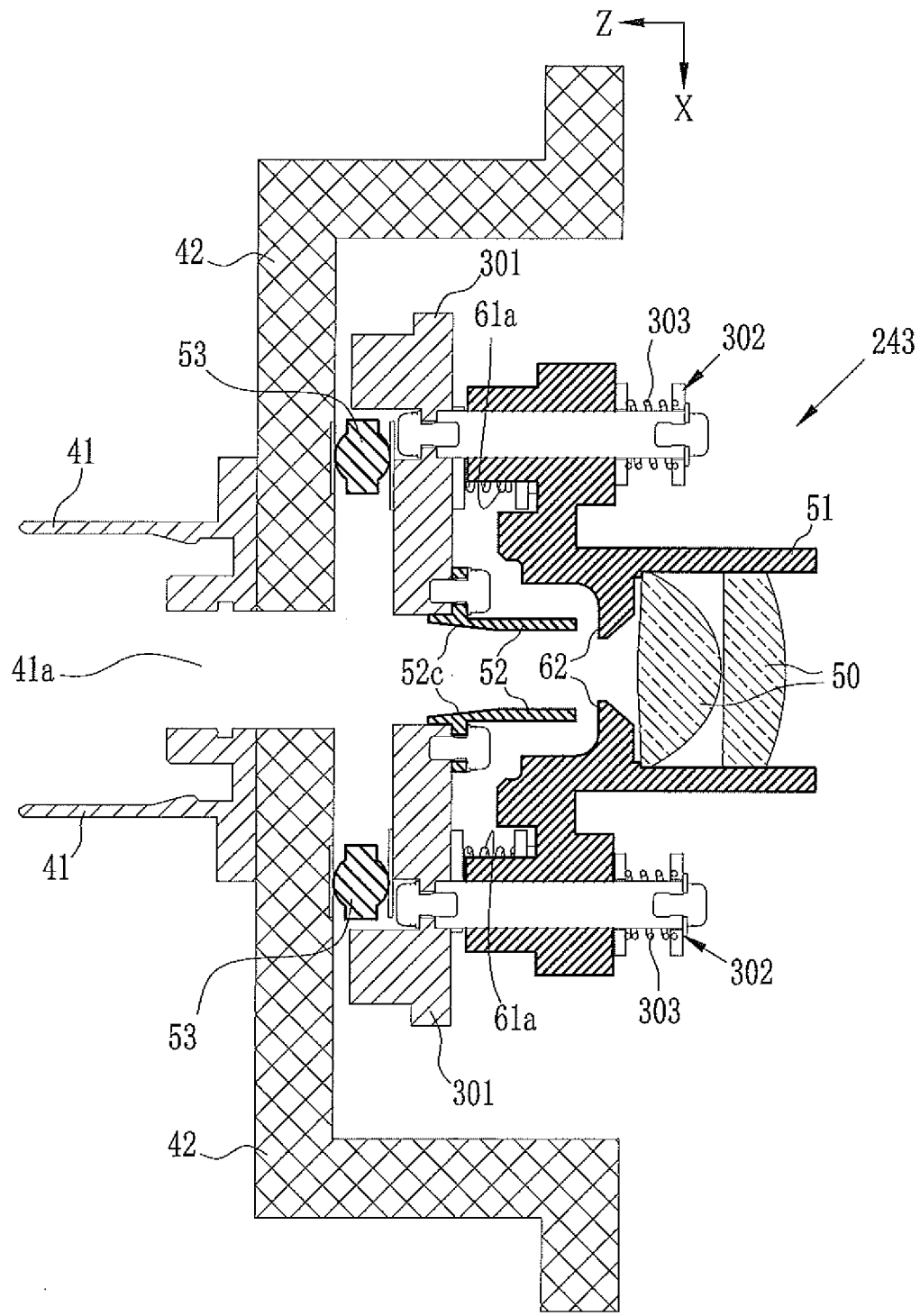
FIG. 17 is a cross-sectional view of the follow mechanism according to the second embodiment.
Figure 18:
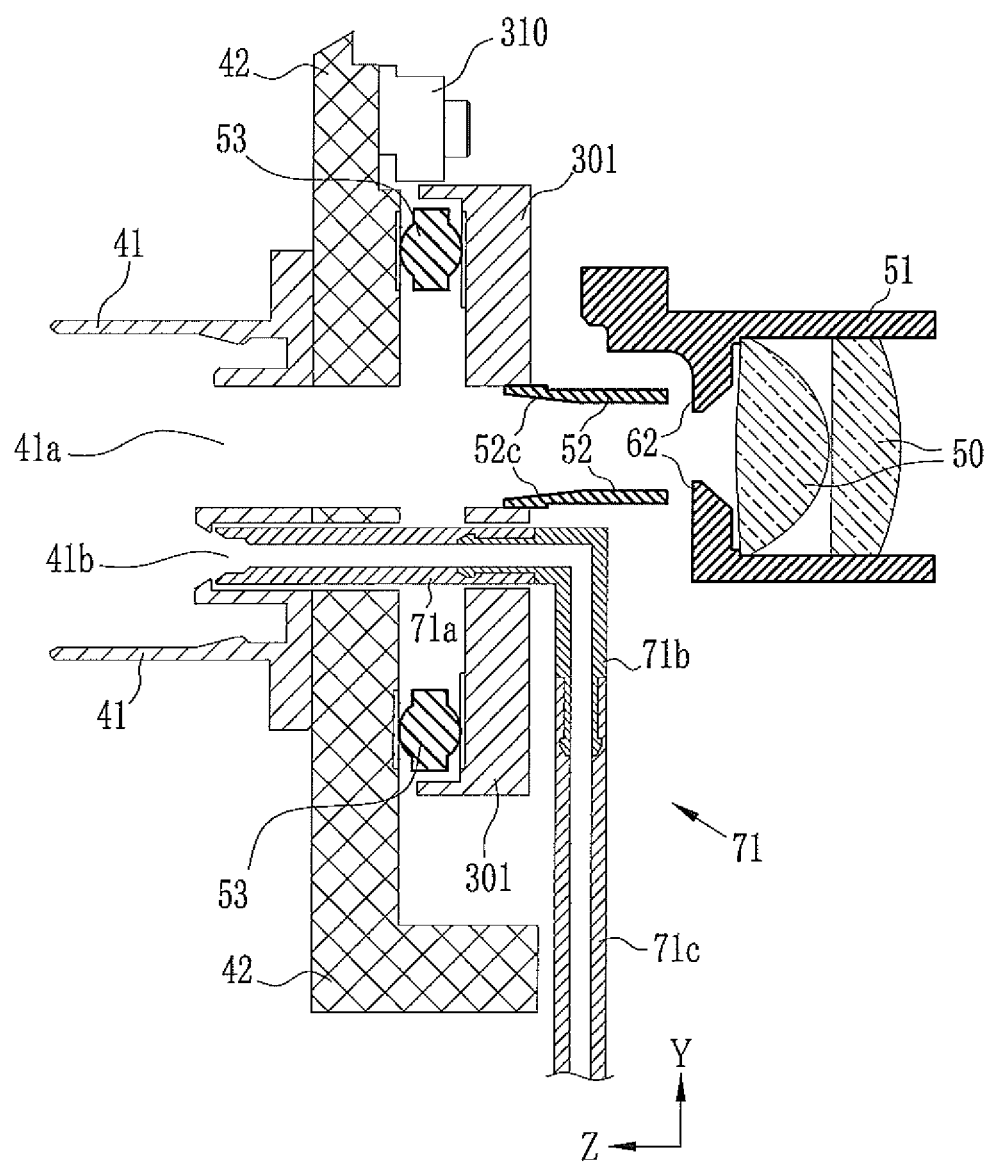
FIG. 18 is a cross-sectional view of the follow mechanism according to the second embodiment.

In the first embodiment, the follow mechanism 43 is provided to the front portion 44a of the light source unit 44. As shown in FIGS. 16 to 18, a follow mechanism 243, which is similar to the follow mechanism 43 of the first embodiment, may be provided to the fitting mount 42. Hereinafter, configuration of the follow mechanism 243 is described. Like reference numerals identify parts having functions similar to those of the follow mechanism 43 of the first embodiment even if the parts are different in shape from those of the follow mechanism 43, and descriptions thereof are omitted.

In the follow mechanism 43 according to the first embodiment, the flange 51b of the lens barrel 51 is fastened to the front portion 44a of the light source unit 44 through the ball member 53. As illustrated in FIG. 17, in the follow mechanism 243 according to the second embodiment, the lens barrel 51 is fastened to a floating plate 301, and the floating plate 301 is fastened to the fitting mount 42 by the mounting unit 61 through the ball member 53. The floating plate 301 corresponds to the flange 51b of the first embodiment, and is movable in the XY direction (the XY in-plane direction perpendicular to the insert direction of the light guide 25). The lens barrel 51 is fastened to the floating plate 301 by a joining unit 302. The receiving unit 52 is fastened to the floating plate 301. The joining unit 302 has a coil spring 303 between the joining unit 302 and the floating plate 301. The joining unit 302 biases the lens barrel 51 toward the floating plate 301 side with the use of the coil spring 303. For this reason, in the follow mechanism 243, the lens barrel 51 is movable in the Z direction (the insertion direction of the light guide 25) relative to the floating plate 301. Thus the impact of the light guide 25 coming in contact with the stop member 62 is reduced. Since the lens barrel 51 is movable in the Z direction, the relative position between the lens 50 and the light guide 25 is finely and optimally adjusted. As a result, the incidence efficiency of the illumination light 90 into the light guide 25 is maintained.

Note that, as illustrated in FIGS. 16 and 18, in the follow mechanism 243, bias members 310 and 311 are provided instead of the bias members 110 and 111 of the first embodiment. The bias force of the bias members 310 and 311 is balanced with the bias force of the bias members 113 and 114 and the gravity acting on the follow mechanism 243. The bias force of the bias members 113, 114, 310, and 311 keeps the position of the center axis 100 of the receiving unit 52 coincident with the center 99 of the illumination light 90 against the gravity.

Note that, in the follow mechanism 243 according to the second embodiment, the lens barrel 51, the floating plate 301, and the joining unit 302 connecting the lens barrel 51 to the floating plate 301 constitute a movable unit. The fitting mount 42 functions as a reference (reference unit) with respect to which the follow mechanism 43 moves.

In the second embodiment, the receiving unit 52 is located behind the light guide insertion opening 41a. Instead, the receiving unit 52 according to the second embodiment may protrude (or extend) to reach the light guide insertion opening 41a. There is known the endoscope 12 having the light guide 25 with its diameter tapered toward the light source device 14. In the case of the endoscope 12 with the tapered light guide 25, it is preferred that the receiving unit 52 protrudes to reach the light guide insertion opening 41a so as to hold the light guide 25 at a portion with the largest diameter on the universal cord 17 side.

Various changes and modifications are possible in the present invention and may be understood to be within the present invention.

What is claimed is:

1. A light source device for an endoscope system having a light source unit, the light source unit applying collimated light to a lens which collects light and allows the collected light to enter a light guide provided to an endoscope, the light source device comprising:
    a receiving unit for receiving insertion of the light guide, the receiving unit having a taper portion for guiding the light guide; and
    a movable unit to which the receiving unit and the lens are attached, the movable unit receiving a force which contains a component in a direction perpendicular to a direction of the insertion of the light guide by the light guide coming in contact with the taper portion, the force moving the lens together with the receiving unit and the movable unit with respect to the light source unit in a direction perpendicular to a direction of the insertion of the light guide and collecting at least a part of the collimated light to the light guide.

2. The light source device according to claim 1, wherein the receiving unit, the movable unit, and the lens move in accordance with the force received by the receiving unit from the light guide due to the light guide coming in contact with the taper portion.

3. The light source device according to claim 1, further comprising:
    a reference unit situated in a predetermined location relative to the collimated light, the movable unit moving with respect to the reference unit;
    a ball member rotatably provided between the reference unit and the movable unit; and
    a mounting unit for movably attaching the movable unit to the reference unit through the ball member.

4. The light source device according to claim 3, further comprising a first bias member for biasing the movable unit toward the reference unit.

5. The light source device according to claim 3, further comprising a second bias member for supporting the movable unit relative to the reference unit and biasing a center position of the receiving unit toward a specific position.

6. The light source device according to claim 1, further comprising:
    a source-side channel provided to the light source device and connected to an endoscope-side channel provided to the endoscope, the endoscope-side channel protruding parallel to the light guide, and
    a flexible connector provided to the source-side channel, the flexible connector being bent, in accordance with a position of insertion of the endoscope-side channel, to receive the insertion of the endoscope-side channel.

7. The light source device according to claim 6, wherein the flexible connector is provided in a channel connecting hole; and there is a space, between the flexible connector and an inner wall of the channel connecting hole, which allows for bending of the flexible connector.

* * * * *